United States Patent [19]
Archibald et al.

[11] Patent Number: 5,362,848
[45] Date of Patent: Nov. 8, 1994

[54] PREPARATION AND POLYMERIZATION OF INITIATORS CONTAINING MULTIPLE OXETANE RINGS: NEW ROUTES TO STAR POLYMERS

[75] Inventors: Thomas G. Archibald; Roland P. Carlson, both of Fair Oaks; Aslam A. Malik, Cameron Park; Gerald E. Manser, El Dorado Hills, all of Calif.

[73] Assignee: Aerojet-General Corporation, Rancho Cordova, Calif.

[21] Appl. No.: 989,401

[22] Filed: Dec. 11, 1992

[51] Int. Cl.$^5$ .............................................. C08G 65/04
[52] U.S. Cl. ................................... 528/414; 528/415; 528/416; 528/417
[58] Field of Search ................. 528/414, 415, 416, 417

[56] References Cited

U.S. PATENT DOCUMENTS

| | | | |
|---|---|---|---|
| H991 | 11/1991 | Fischer | 549/510 |
| 2,722,340 | 11/1955 | Feild | 220/457 |
| 2,895,922 | 7/1959 | Goddu | 528/416 |
| 3,058,994 | 10/1962 | Schrage | 549/510 |
| 3,112,280 | 11/1963 | Farthing | 528/408 |
| 3,462,454 | 8/1969 | Gartner | 549/511 |
| 4,395,561 | 7/1983 | Baum | 549/510 |
| 4,405,762 | 9/1983 | Earl | 525/410 |
| 4,560,779 | 12/1985 | Guimont | 549/510 |
| 4,683,086 | 7/1987 | Frankel | 260/349 |
| 4,707,540 | 11/1987 | Manser | 528/417 |
| 4,952,644 | 8/1990 | Wardle et al. | 525/410 |

FOREIGN PATENT DOCUMENTS 758450 10/1956 United Kingdom ............... 528/408

*Primary Examiner*—John Kight, III
*Assistant Examiner*—Richard Jones
*Attorney, Agent, or Firm*—Townsend and Townsend Khourie and Crew

[57] ABSTRACT

This invention relates to novel multifunctional oxetanes, i.e., compounds having multiple oxetane groups, which are useful as initiators in the preparation of star polymers and polymer cascades containing energetic groups. In addition, this invention relates to a process for the preparation of star polymers and polymer cascades, whereby novel multifunctional oxetanes act as initiators in the formation of theses polymers. The reaction of these initiators with various propagating, high-energy oxetanes, such as 3,3-bis-(azidomethyl)oxetane (BAMO) and 3-nitratomethyl-3-methyloxetane (NMMO), gives star polymers with varying molecular weights and functionalities. The star polymers and polymer cascades of the present invention are useful as binders in high-energy formulations.

10 Claims, No Drawings

PREPARATION AND POLYMERIZATION OF INITIATORS CONTAINING MULTIPLE OXETANE RINGS: NEW ROUTES TO STAR POLYMERS

FIELD OF THE INVENTION

This invention relates to novel multifunctional oxetanes, i.e., compounds having multiple oxetane groups, which are useful as initiators in the preparation of star polymers and polymer cascades containing energetic groups. In addition, this invention relates to a process for the preparation of star polymers and polymer cascades, whereby multifunctional oxetanes act as initiators in the formation of these polymers. The reaction of multioxetane initiators with various propagating, high-energy oxetanes, such as 3,3-bis-(azidomethyl)oxetane (BAMO) and 3-nitratomethyl-3-methyloxetane (NMMO), gives star polymers with varying molecular weights and functionalities. The star polymers of the present invention are useful as binders in high-energy formulations, such as propellants, explosives, gasifiers, or the like.

BACKGROUND OF THE INVENTION

High energy solid formulations, such as propellants, explosives, and gasifiers, generally consist of particulate solids, such as fuel materials, oxidizers, or both, held together by an elastomeric binder. These high-energy formulations may also include a liquid plasticizer, such as a nitrate ester, which contributes to the elastomeric characteristic of the binder and adds additional energy to the formulation.

Conventional binders for high-energy formulations utilize cross-linked elastomers in which prepolymers are polyethers derived from oxetane compounds. Oxetanes can be substituted at the 3-position with methyl groups containing energetic functional groups such as nitro, nitrato, azido, and difluoroamino groups. Polyethers can be formed from these oxetane compounds by cationic polymerization. This technique employs an initiator formed from an adduct of an organic compound such as a diol (e.g., 1,4-butanediol) and a catalyst capable of causing cationic polymerization. Such catalysts include strong acids or Lewis acids. Once formed, the initiator reacts with one of the available oxetane monomers to form an initiating species, and polymerization proceeds by chain elongation until substantial, e.g., greater than about 95%, exhaustion of the monomers. Cationic polymerization of these oxetane compounds gives a hydroxy terminated polymer with a load bearing polyether backbone and pendant energetic groups.

Since these polymers are hydroxy-terminated, they are curable with isocyanates through chain extension and cross-linkable to form elastomers. Elastomers are formed from these polyethers by curing with isocyanates having a functionality of at least two, e.g., toluene diisocyanate. In order to obtain adequate mechanical properties, some degree of cross-linking of the polymer chains is required. Cross-linking is promoted by using an isocyanate of higher functionality or by adding a separate crosslinking agent, such as trimethylolethane or trimethylolpropane.

Despite the general teaching that these cross-linked elastomers are useful as binders in high-energy formulations, there are some important disadvantages to using them as binders. Cross-linked elastomers, for example, must be cast within a short period of time after addition of the curative. Additionally, disposal of a cast, cross-linked propellant formulation is very difficult, except by burning, which poses environmental problems and concerns. These cross-linked elastomers, therefore, are difficult to use in continuous processing, and they present a problem for removal during demilitarization.

In view of the inherent disadvantages of using cross-linked elastomeric polyethers as binders, attempts have been made to use oxetane monomers to prepare thermoplastic elastomers (TPEs) suitable for use as binders in high-energy formulations. High-energy oxetane monomers which are symmetrically di-substituted at the 3-position, such as 3,3-bis-(azidomethyl)oxetane (BAMO) or 3,3-bis-(nitratomethyl)oxetane (BNMO), give crystalline polymers known as hard blocks. Asymmetrically substituted oxetane monomers, such as 3-azidomethyl-3-methyloxetane (AMMO) or 3-nitratomethyl-3-methyloxetane (NMMO), give amorphous homopolymers known as soft blocks. Sequential polymerization of soft and hard block materials to give ABA block polymers by conventional methods have not given TPEs with useful properties. The use of low temperatures, dilute solutions, and bis-(cumyl chloride) catalysts have resulted in thermoplastic, elastomeric ABA block polymers with good mechanical properties suitable for use as binders in high-energy formulations, but these TPEs do not appear to be economically practical.

Star polymers contain several homopolymers attached at a single, central point and as a result, polymer chain-entanglement and crystallinity are radically altered. Star polymers and copolymers formed from oxetane compounds give materials having mechanical properties which make them useful as binders in high-energy formulations. Previous attempts to prepare star polymers by conventional multifunctional alcohol-boron trifluoride initiation, however, have not given materials with very useful properties.

In view of the foregoing, there exists a need for a novel method of preparing star polymers and polymer cascades having properties suitable for use as binders in high-energy formulations, such as propellants, gasifiers, or explosives.

SUMMARY OF THE INVENTION

In accordance with the present invention, multioxetane compounds, i.e., compounds having two or more oxetane rings joined together in a single molecule, are produced. These multioxetane compounds are prepared using the Williamson Ether Synthesis which involves the reaction of an alkoxide with an organic halide. It has now been discovered that these compounds are useful as initiators in the preparation of star polymers and polymer cascades. Each oxetane ring can initiate a polymer chain such that difunctional oxetane monomers will give star polymers with two branches, trifunctional oxetane monomers will give star polymers with three branches, tetrafunctional oxetane monomers will give star polymers with four branches, and so on.

This invention further relates to a process for the preparation of star polymers and polymer cascades. This process involves the formation of an initiator compound by reacting a preinitiator precursor, e.g., a diol, with a catalyst effective for cationic polymerization. Once formed, this initiator compound is reacted with a multioxetane compound to form an initiating species. The initiating species is combined with a monomer capable of cationic polymerization, and polymerization is allowed to proceed by chain elongation until the supply of available monomer is substantially exhausted. The star polymers and polymer cascades of the present invention are useful as binders in high-energy formulations, such as propellants, explosives, gasifiers, or the like.

Conventional binders for high-energy formulations utilize cross-linked elastomers in which prepolymers are polyethers derived from oxetane derivatives substituted at the 3-position with energetic pendant groups. The polyether chains contain hydroxy functionalities which are curable with isocyanates. In order to obtain adequate mechanical properties, some degree of cross-linking of the polymer chains is required. This is accomplished through the use of a trifunctional isocyanate or by increasing the hydroxy functionality of the polymer by termination with a triol such as trimethylolethane or trimethylolpropane in the case of oxetane polymers. This method requires three chemical reactions in close proximity to effect the cross-link, a difficult problem in the presence of high solid loading such as is found in propellant applications.

In the case of a star polymer or polymer cascade, however, several polymer chains are started at a common site and each chain terminates with a hydroxy functionality. Since each star polymer may have three or more hydroxy groups, crosslinking occurs when cured with a diisocyanate, e.g., toluene diisocyanate. Additionally, since the hydroxy groups of a star polymer are at the end of the chains, far from the branching points, there is no congestion. Curing reactions of star polymers are, in essence, simple chain extensions which result in the formation of improved network structures.

The oxetane star polymers of the present invention contain multiple polyether chains attached at a single, central point and as a result, chain-entanglement and polymer crystallinity are radically altered. The initiating species, and thus the branching points, can be selected from various structures containing at least two or more oxetane groups joined together at a single point. The reaction of these initiators with various propagating, high-energy oxetane monomers, such as, for example, 3,3-bis-(azidomethyl)oxetane (BAMO) and 3-nitratomethyl-3-methyloxetane (NMMO), produce star polymers with varying molecular weights and functionalities. The use of multioxetane compounds in the formation of star polymers provides a means of gaining control over the cross-link density and the network topology of the cured binder. Multioxetane initiated star polymers can be easily modified to meet performance requirements.

Other advantages, objects, features and embodiments of the present invention will become apparent from the detailed description which follows.

DETAILED DESCRIPTION OF THE INVENTION AND PREFERRED EMBODIMENTS

Multioxetane compounds in accordance with the present invention include those having the general formula:

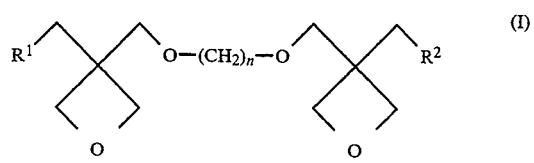

In the above formula, $R^1$ and $R^2$ are independently selected and may be functional groups including, but not limited to, H, lower alkyl, lower alkoxy, Br, Cl, I, $NF_2$, $ONO_2$, $NO_2$, $N_3$, and $N(R^3)NO_2$, where $R^3$ is H or a lower alkyl. The term "independently selected" is used herein to indicate that the two R groups, $R^1$ and $R^2$, may be identical or different. The term "alkyl" is used herein to refer to substitutents that are saturated hydrocarbon radicals. The alkyl groups may be straight-chain or branched-chain, limited only by steric hinderance. Additionally, since alkyl groups do not contribute to the energetic character of the molecule, shorter alkyl groups (i.e., 1–4 carbon atoms) are preferred. The term "alkoxy" is used herein to refer to an alkyl radical which also bears an oxygen substituent that is capable of covalent attachment to another hydrocarbon radical (e.g., a methoxy or ethoxy group). As with alkyl groups, shorter alkoxy groups are preferred. The symbol "n" represents an integer having a value ranging from 1 to about 10.

Within the scope of Formula I, certain embodiments are preferred, namely those in which $R^1$ and $R^2$ are independently selected from the following functional groups: H, Cl, I, $NO_2$, $ONO_2$, and $N_3$; and n is an integer having a value of 4 or 6. Further preferred are multioxetane compounds in which $R^1$ and $R^2$ are both either H or Cl; and n has a value of 4 or 6. Also preferred are multioxetane compounds in which $R^1$ and $R^2$ are both either $ONO_2$ or $N_3$; and n has a value of 4, 6 or 8.

Multioxetane compounds in accordance with the present invention also include those having the general formula:

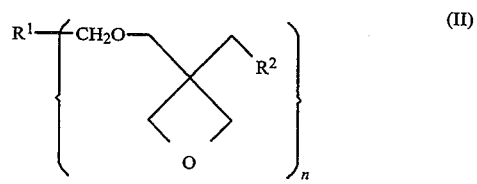

In Formula II, $R^1$ is a lower alkyl with a valence of n. $R^2$ is independently selected and is a functional group including, but not limited to, H, lower alkyl, lower alkoxy, Br, Cl, I, $NF_2$, $ONO_2$, $NO_2$, $N_3$, and $N(R^3)NO_2$, where $R^3$ is H or a lower alkyl. The symbol "n" is an integer having a value of 2, 3, or 4. Within the scope of Formula II, certain multioxetane compounds are preferred. The multioxetane compound in which $R^1$ is C; $R^2$ is H; and n is 4 is preferred. Also preferred is the multioxetane compound in which $R^1$ is $CH_3CH_2C$; $R^2$ is H; and n is 3.

Multioxetane compounds in accordance with the present invention further include those having the general formula:

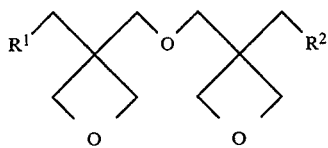
(III)

In the above formula, R¹ and R² are independently selected and may be functional groups including, but not limited to, H, lower alkyl, lower alkoxy, Br, Cl, I, $NF_2$, $ONO_2$, $NO_2$, $N_3$, and $N(R^3)NO_2$, where R³ is H or a lower alkyl. Within the scope of Formula III, certain embodiments are preferred, namely those in which R¹ and R² are independently selected from the following functional groups: H, $NO_2$, $ONO_2$, and $N_3$. Further preferred is the multioxetane compound in which R¹ and R² are both H.

In addition, multioxetane compounds in accordance with the present invention include those having the general formula:

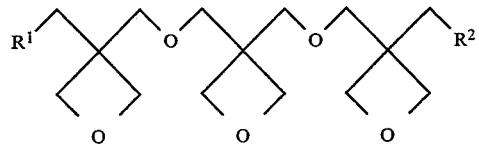
(IV)

In Formula IV, R¹ and R² are independently selected and may be functional groups including, but not limited to, H, lower alkyl, lower alkoxy, Br, Cl, I, $NF_2$, $ONO_2$, $NO_2$, $N_3$, and $N(R^3)NO_2$, where R³ is H or a lower alkyl. Within the scope of the above formula, certain embodiments are preferred, namely those in which R¹ and R² are independently selected from the following functional groups: H, $NO_2$, $ONO_2$, and $N_3$. Further preferred is the multioxetane compound in which R¹ and R² are both H.

The multioxetane compounds of the present invention can be prepared using the Williamson Ether Synthesis which involves the reaction of an alkoxide with an organic halide. The first step in the reaction involves the formation of an alkoxide. For example, the reaction of 3-hydroxymethyl-3-methyloxetane (HMMO) with sodium hydride in dimethylformamide (DMF) gives the sodium salt of HMMO (1). Other bases, such as butyl lithium, and other solvents, such as ether amides or sulfoxides, can also be used. The sodium salt of HMMO can be used in situ as prepared or it can be isolated and stored as a dry solid.

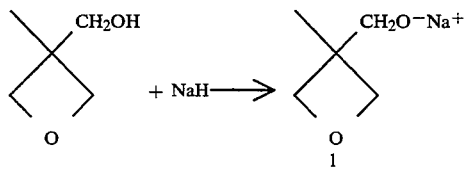

Reaction of the sodium salt of HMMO with various alkyl bromides at 80° C.–120° C. in DMF gives multioxetane compounds corresponding to Formula II. For example, reaction of the sodium salt of HMMO with 1,1,1-tris-(bromomethyl)propane gives 1,1,1-tris-[(3-methyl-3-oxetanyl)methyloxymethyl]propane (TOX) (2), and with tetrakis-(bromomethyl)methane it gives tetrakis-[3-methyl-3-oxetanyl)methyloxymethyl]methane (3). Although alkyl bromides are the organic halides used in the presently preferred embodiment, it will be readily apparent to the skilled artisan that other alkyl chlorides, iodides and tosylates can also be used.

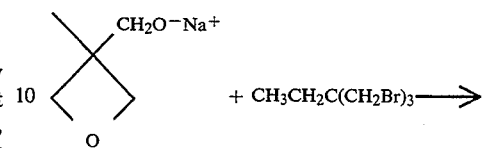

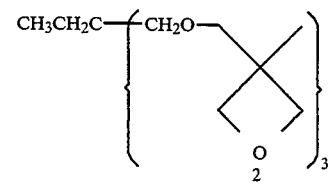

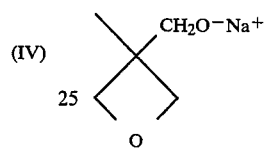

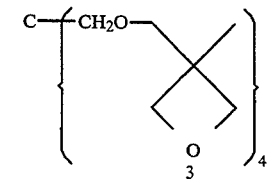

More closely spaced multioxetane initiators, corresponding to Formulas III and IV, can be prepared by reacting the HMMO salts with oxetanes containing displaceable groups. For example, the reaction of the sodium salt of HMMO with 3-hydroxymethyl-3-methyloxetane p-toluenesulfonate gives 3-methyl-3-[(3-methyl-3-oxetanyl)methyloxymethyl]oxetane (4), and with 3,3-bis-(chloromethyl)oxetane it gives 3,3-bis-[(3-methyl-3-oxetanyl)methyloxymethyl]oxetane (5).

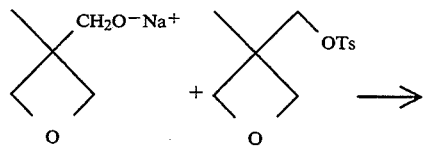

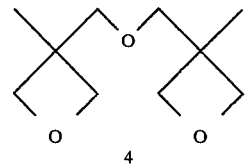

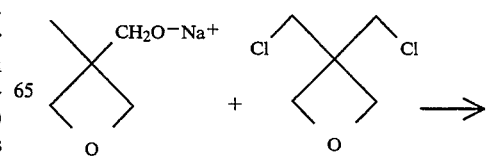

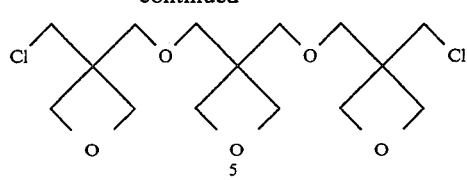

Multioxetane compounds, corresponding to Formula I, can have oxetane groups connected with aliphatic or aromatic groups. For example, the reaction of the sodium salt of HMMO with 1,4-dibromobutane or 1,6-dibromohexane give the initiators 1,4-bis-[(3-methyl-3-oxetanyl)methyloxy]butane (6, wherein n=4) and 1,6-bis-[(3-methyl-3-oxetanyl)methyloxy]hexane (6, wherein n=6), respectively. In the case of the straight-chain, primary aliphatic halides, significant reduction in the yield of the multioxetane compound is caused by an elimination reaction which forms the monofunctional oxetane-olefins, such as, for example, 1-[(3-methyl-3-oxetanyl)methyloxy]hex-5-ene (7).

bis-[3-methyl-3-oxetanyl)methyloxy]hexane (9, wherein n=6).

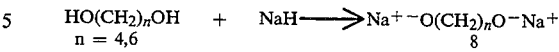

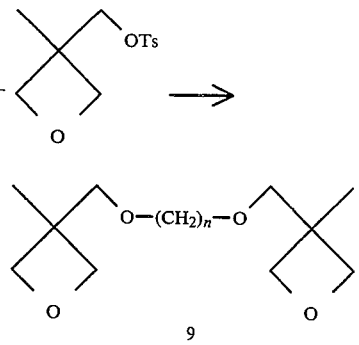

Reaction of the disodium salt of butane 1,4-diol with

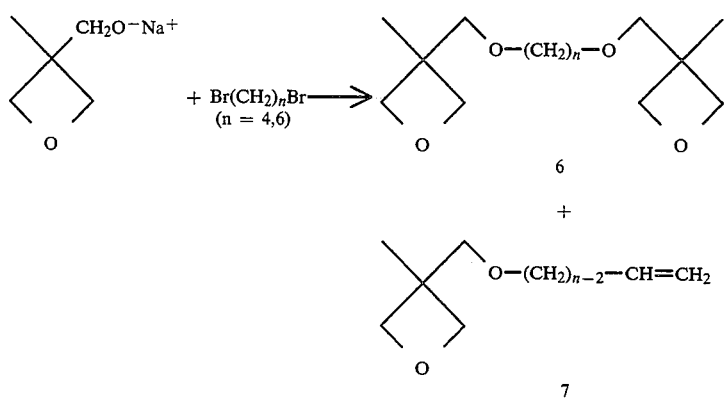

The multioxetanes from straight-chain aliphatic compounds can be prepared in high yield, however, by reacting the alkoxides of straight-chain diols with halo or tosyl derivatives of 3-methyloxetane. For example, the reaction of butane-1,4-diol with sodium hydride in DMF gives the corresponding 1,4-dialkoxide (8). Reaction of the dialkoxide with 3-hydroxymethyl-3-methyloxetane p-toluenesulfonate gives 1,4-bis-[3-methyl-3-oxetanyl)methyloxy]butane (9, wherein n=4). Similarly, reaction of the 1,6-dialkoxide with 3-hydroxymethyl-3-methyloxetane p-toluenesulfonate gives 1,6- excess 3,3-bis-(chloromethyl)oxetane gives 1,4-bis-[(3-chloromethyl-3-oxetanyl)methyloxy]butane (10). This difunctional oxetane can be further substituted to give multioxetane compounds having various pendant groups. Substitution of the difunctional oxetane can be tailored so that the multioxetane compound can react with oxetane monomers having widely varying reactivity ratios. Reaction of 1,4-bis-[(3-chloromethyl-3-oxetanyl)methyloxy]butane with sodium iodide gives 1,4-bis-[3-iodomethyl-3-oxetanyl)methyloxy]butane (11). Reaction of this diiodide with silver nitrate gives 1,4-bis-[(3-nitratomethyl-3-oxetanyl)methyloxy]butane (12), and with sodium azide it gives 1,4-bis-[(3-azidomethyl-3-oxetanyl)methyloxy]butane (13).

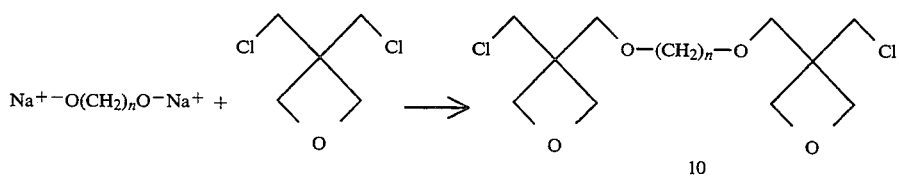

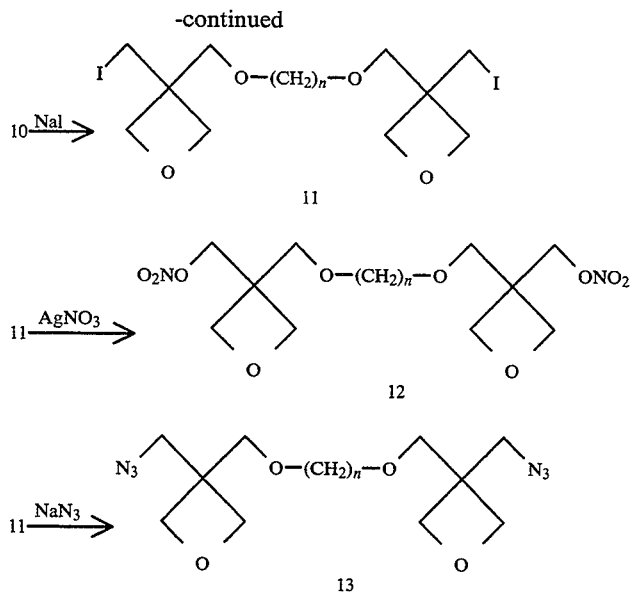

This methodology can be used to introduce other energetic pendant groups, including, but not limited to, nitroamino, nitro, difluoroamino and cubyl, into the multioxetane compounds. Non-energetic derivatives such as ethoxy or methoxy can be similarly prepared. The use of tri- or tetrafunctional alkoxides with 3,3-bis-(chloromethyl)oxetane gives the entry point to functionalized multioxetane compounds having more than three oxetane groups. The use of cascading alcohols can give initiators with unlimited numbers of oxetanes attached.

The invention further resides in a process for the preparation of star polymers and polymer cascades. The process involves: (a) forming an initiator compound by reacting a preinitiator precursor with a catalyst, said preinitiator precursor being an organic compound capable of forming an adduct with said catalyst, and said catalyst being a substance capable of causing cationic polymerization; (b) combining said initiator compound with a multioxetane compound to form an initiating species; (c) contacting said initiating species with a monomer capable of cationic polymerization; and (d) allowing polymerization to proceed by chain elongation until the supply of available monomer is substantially exhausted.

In the process of the present invention, certain terms used are defined as follows. The term "preinitiator precursor" is used herein to refer to an organic compound which forms, with a catalyst, an adduct or complex, such adduct or complex being an initiator. The term "catalyst" is used herein to refer to a substance, typified by a Lewis acid, e.g., $BF_3$, which is capable of catalyzing cationic polymerization. The term "initiator" or "initiator compound" is used herein to refer to an adduct of an organic compound with a catalyst which results, when brought into contact with a multioxetane compound, in the formation of an initiating species which starts (initiates) the formation of a polymer chain(s). The term "multioxetane compound" is used herein to refer to a compound having two or more oxetane rings joined together in the same molecule. The term "monomer" is used herein to refer to a simple molecule which is capable of cationic polymerization. The term "living polymer" is used herein to refer to the positively charged (cationic) chain(s) resulting from the reaction of a multioxetane initiating species with a monomer.

The preinitiator precursor used in the process of the present invention may be chosen from those known in the art, including, but not limited to, mono- and polyhydric alcohols, such as butane-1,4-diol, propane-1,3-diol, trifluoroethanol, trimethylolethane. In the presently preferred embodiment, the preinitiator precursor used is either butane-1,4-diol or trifluoroethanol. The acid catalyst may also be selected from those known in the art, including Lewis acids, such as $AlCl_3$, $BF_3$, $TiCl_4$, $ZnI_2$, $SiF_4$, $SbF_6$, $PF_5$, $AsF_5$, and $SbCl_5$, and strong acids, such as $FSO_3H$, $ClSO_3H$, $HClO$, $HIO$, and $CF_3SO_3H$. In the presently preferred embodiment, the acid catalyst used is $BF_3$. Boron trifluoride ($BF_3$) may be mixed first with butane-1,4-diol or trifluoroethanol to form the initiator compound, or it may be used in the form of its etherate in which event the butane-1,4-diol or the trifluoroethanol displaces the ether to form the initiator. In either case, a butane-1,4-diol/$BF_3$ adduct or a trifluorethanol/$BF_3$ adduct is formed, and it serves as the initiator for the overall polymerization reaction.

The multioxetane compound used in the process of the present invention may be selected from the following compounds:

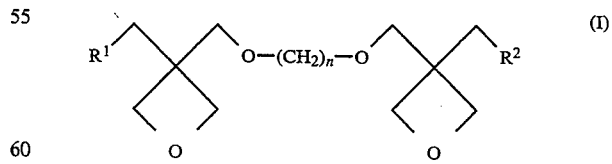

in which $R^1$ and $R^2$ are independently selected and may be functional groups including, but not limited to, H, lower alkyl, lower alkoxy, Br, Cl, I, $NF_2$, $ONO_2$, $NO_2$, $N_3$, and $N(R^3)NO_2$, where $R^3$ is H or a lower alkyl; and n is an integer having a value ranging from 1 to 10;

OR

-continued

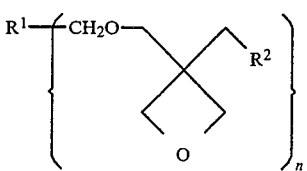

(II)

in which $R^1$ is a lower alkyl with a valence of n; $R^2$ is independently selected and is a functional group including, but not limited to, H, lower alkyl, lower alkoxy, Br, Cl, I, $NF_2$, $ONO_2$, $NO_2$, $N_3$, and $N(R^3)NO_2$, where $R^3$ is H or a lower alkyl; and n is an integer having a value of 2, 3, or 4;

OR

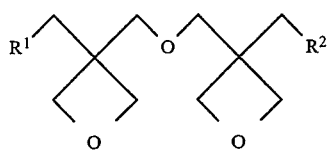

(III)

in which $R^1$ and $R^2$ are independently selected and may be functional groups including, but not limited to, H, lower alkyl, lower alkoxy, Br, Cl, I, $NF_2$, $ONO_2$, $NO_2$, $N_3$, and $N(R^3)NO_2$, where $R^3$ is H or a lower alkyl;

OR

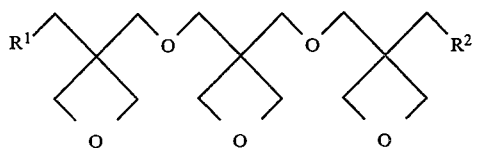

(IV)

in which $R^1$ and $R^2$ are independently selected and may be functional groups, including, but not limited to, H, lower alkyl, lower alkoxy, Br, Cl, I, $NF_2$, $ONO_2$, $NO_2$, $N_3$, and $N(R^3)NO_2$, where $R^3$ is H or a lower alkyl.

The monomers used in the present invention are those which are susceptible to cationic polymerization. Cyclic ethers having three, four, and five membered rings, which are characterized by ring strain, are susceptible to this type of polymerization. In particular, oxetane monomers are the cyclic ethers used in the process of the present invention. The oxetane monomers used have the general formula:

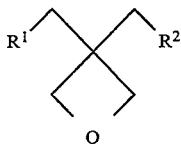

in which $R^1$ and $R^2$ are independently selected and may be functional groups including, but not limited to, H, lower alkyl, lower alkoxy, Br, Cl, I, $NF_2$, $ONO_2$, $NO_2$, $N_3$, and $N(R^3)NO_2$, where $R^3$ is H or a lower alkyl. Examples of oxetanes used to form star polymers in accordance with the invention include, but are not limited to, the following:

BEMO 3,3-bis-(ethoxymethyl)oxetane,
BCMO 3,3-bis-(chloromethyl)oxetane,
BMMO 3,3-bis-(methoxymethyl)oxetane,
BFMO 3,3-bis-(fluoromethyl)oxetane,
HMMO 3-hydroxymethyl-3-methyloxetane,
BAOMO 3,3-bis-(acetoxymethyl)oxetane,
BHMO 3,3-bis-(hydroxymethyl)oxetane,
OMMO 3-octoxymethyl-3-methyloxetane,
CMMO 3-chloromethyl-3-methyloxetane,
AMMO 3-azidomethyl-3-methyloxetane,
BIMO 3,3-bis-(iodomethyl)oxetane,
IMMO 3-iodomethyl-3-methyloxetane,
PMMO 3-propynomethyl-3-methyloxetane,
NMMO 3-nitratomethyl-3-methyloxetane,
BMNAMO 3,3-bis-(methylnitratomethyl)oxetane,
MNAMMO 3-methylnitratomethyl-3-methyloxetane, and
BAMO 3,3-bis-(azidomethyl)oxetane.

Any solvent known to be compatible with cationic polymerization with respect to solubility of reactants, stability of the cations formed on initiation, etc., may be used. Methylene chloride is the solvent used in the presently preferred embodiment of the present invention, however, other solvents such as chloroform, hexane, or carbon tetrachloride may also be used.

The polymerization reaction is carried out in the absence of any substance which would prevent or prematurely terminate the reaction. Water, for example, should be excluded. The time required to complete or substantially complete polymerization will depend upon the reactants and the catalyst used. Polymerization will proceed until substantial exhaustion of the cyclic ether monomer or until the reaction is terminated in some other manner. The resulting living polymers (cations) making up the star polymer may be terminated in a number of different ways. Termination may be accomplished by adding water to produce terminal hydroxy groups; by adding ammonia or an amine to produce terminal amino groups ( e.g., $NH_2$ from ammonia or $-NHCH_3$ from methyl amine); by adding a carboxylic acid or its salt to produce a terminal ester group ( e.g., addition of acetic acid produces an acetate group, $CH_3COO-$); or by adding a mineral acid such as HCl, $H_2SO_4$ or HF to produce terminal chlorine, sulfate or fluorine atoms or groups. In general, any terminating species known to terminate living cationic polymers may be used. In the preferred embodiment of the present invention, the living polymers making up the star polymer are terminated by quenching the reaction with water and thus, terminal hydroxy groups are produced.

In the case of a star polymers, several polyether chains are started at a single, central point and each chain terminates in a hydroxy functionality. Since each star polymer may have two or more hydroxy groups, cross-linking of the polyether chains occurs when the star polymer is cured with a diisocyanate, e.g., toluene diisocyanate. Additionally, since the hydroxy groups of a star polymer are at the end of the chains, far from the branching points, there is no congestion. Curing reactions of star polymers are, in essence, simple chain extensions which result in the formation of improved network structures.

The multioxetane compounds used in the process of the present invention can be tailored to meet the widely varying reactivity requirements of the oxetane monomers which are suitable for use in the process of the present invention. Multioxetane compounds containing no electron-withdrawing groups are more reactive than the multioxetane compounds containing azidomethyl and nitratomethyl pendant groups, and these compounds can be used to initiate star polymers formed from oxetane monomers containing either energetic or non-energetic pendant groups. For example, 3-nitratomethyl-3-methyloxetane (NMMO) was initiated with 1,1,1-tris-[(3-methyl-3-oxetanyl)methyloxymethyl]propane (TOX) using a butane-1,4-diol/BF$_3$ complex to give a star polymer having a molecular weight of 4,368 and a polydispersity of 1.47. Similarly, 3,3-bis-(ethoxymethyl)oxetane was initiated with 1,6-bis-[(3-methyl-3-oxetanyl)methyloxy]hexane to give a star polymer having a molecular weight of 4,368 and a polydispersity of 1.47.

With the less reactive monomers, such as 3,3-bis-(azidomethyl)oxetane, initiation using TOX requires careful regulation of the reaction conditions in order to prevent the homopolymerization of the TOX. Addition of the catalyst followed by the addition of BAMO gave a 26% yield of a polymer with a 2,700 molecular weight and a polydispersity of 1.38. In contrast, when the BAMO and the TOX were premixed and then added to the boron trifluoride catalyst, an 87% yield of a polymer with a molecular weight of 2,800 and a polydispersity of 1.48 was obtained. This polymer was shown by gel permeation chromatography (GPC) to have four components.

To avoid differences in reactivity for the less reactive oxetane monomers, azidomethyl- and nitratomethyl-substituted multioxetane initiators, such as 1,4-bis-[(3-azidomethyl-3-oxetanyl)methyloxy]butane (ADOX), may be used. ADOX was found to form a homopolymer that is highly cross-linked with the boron trifluoride catalyst at −10° C. However, in the presences of other oxetane monomers, such as BAMO or BEMO, star polymers are obtained with molecular weights ranging from about 3,000 to about 7,000.

The invention will be described in greater detail by way of specific examples. The following examples are offered for illustrative purposes, and are intended neither to limit or define the invention in any manner.

EXAMPLE I

This example illustrates the preparation and properties of the initiator 1,1,1-tris-[(3-methyl-3-oxetanyl)methyloxymethyl]propane.

Sodium hydride (50% dispersion in mineral oil, 9.60 g, 0.2 mol) was washed twice with hexanes and was suspended in 200 mL of dimethylformamide (DMF). Then, 3-hydroxymethyl-3-methyloxetane (22.1 g, 0.216 mol) was added dropwise over 45 min while hydrogen gas was evolved and a beige solid precipitated. The mixture was stirred for 30 min and a solution of 1,1,1-tris-(bromomethyl)propane (16.15 g, 0.05 mol) in 190 mL of DMF was added. The mixture was heated to 70° C. for 16 h and 100° C. for 24 h when $^1$H NMR analysis of an aliquot showed that the starting halide had been consumed. The mixture was poured into 500 mL of water and extracted with two portions of 200 mL of methylene chloride. The combined organic extracts were washed with 3 portions of 150 mL of water, dried over magnesium sulfate (MgSO$_4$), passed through silica gel, and evaporated to give 12.5 g, representing a 65% yield, of 1,1,1-tris-[(3-methyl-3-oxetanyl)methyloxymethyl]propane as an oil. The oil was further purified by bulb-to-bulb distillation at 110°–120° C. and 0.25–0.25-mm pressure.

NMR: $^1$H NMR 0.86 (t, J=7.3 Hz, 3H), 1.29 (s, 9H), 1.45 (q, J=7.5 Hz, 2H), 3.36 (s, 2H), 3.42 (s, 2H), 4.32 (d, J=5.5 Hz, 6H); 4.51 (d, J=5.5 Hz, 6H); $^{13}$C NMR 7.566, 21.212, 23.066, 39.826, 43.539, 71.505, 76.176, 79.797. Elemental analysis calculated for C$_{21}$H$_{38}$O$_6$: C, 65.26; H,9.91; Found: C, 65.45; H, 10.07.

EXAMPLE II

This example illustrates the preparation and properties of the initiator tetrakis-[(3-methyl-3-oxetanyl)methoxymethyl]methane.

Sodium hydride (50% dispersion in mineral oil, 16.10 g. 0.33 mol) was washed twice with hexanes and was suspended in 500 mL of DMF. Then, 3-hydroxymethyl-3-methyloxetane (34.2 g, 0.33 mol) was added dropwise over 45 min while hydrogen gas was evolved and a beige solid precipitated. The mixture was stirred for 30 min and a solution of tetrakis-(bromomethyl)methane (25.0 g, 0.0645 mol) in 250 mL of DMF was added. The mixture was heated to 100° C. for 64 h when $^1$H NMR analysis of an aliquot showed that the starting halide had been consumed. The mixture was poured into 500 mL of water and extracted with three portions of 200 mL of methylene chloride. The combined organic extracts were washed with 3 portions of 200 mL of water, dried over magnesium sulfate, and evaporated to give an oil. The oil was cooled to −15° C. for 24 h, and the solid that formed was triturated with ether, filtered, and recrystallized from ethanol to give 6.15 g (21.3%) of tetrakis-[(3-methyl-3-oxetanyl)methoxymethyl]methane, mp 108.5°–109.5° C.

NMR: $^1$H NMR 1.29 (s, 12H), 3.41 (s, 8H), 3.49 (s, 8H), 4.33 (d, J=5.5 Hz, 8H), 4.51 (d, J=5.5 Hz, 8H); $^{13}$C NMR 21.318, 39.95 1, 46.065, 70.097, 76.309, 79.898. Elemental analysis calculated for C$_{25}$H$_{44}$O$_8$: C, 63.53; H, 9.38; Found: C, 63.87; H, 9.26.

EXAMPLE III

This example illustrates the preparation and properties of the initiator 3-methyl-3-[(3-methyl-3-oxetanyl)-methyloxymethyl]oxetane.

Sodium hydride (50% dispersion in mineral oil, 25.15 g, 0.524 mol) was washed twice with hexanes and was suspended in 500 mL of DMF. Then, 3-hydroxymethyl-3-methyloxetane (53.45 g, 0.524 mol) was added dropwise over 45 min while hydrogen gas was evolved and a beige solid precipitated. The mixture was stirred for 30 min and a solution of 3-hydroxymethyl-3-methyloxetane p-toluenesulfonate (103.17 g, 0.403 mol) in 150 mL of DMF was added. The mixture was heated to 100° C. for 64 h when $^1$H NMR analysis of an aliquot showed that the starting sulfonate had been consumed. The mixture was poured into 600 mL of water and extracted with three portions of 200 mL methylene chloride. The combined organic extracts were washed with 3 portions of 200 mL of water, dried over magnesium sulfate, and evaporated to give 68.25 g, representing a 91% yield, of 3-methyl-3-[(3-methyl-3-oxetanyl)methyloxymethyl]oxetane as an oil containing less than 1% of DMF. The oil was distilled at 70° C. and 0.1-mm pressure to give 54.6 g, representing a 78.7% yield, of the analytically pure ether.

NMR: $^1$H NMR 1.31 (s, 6H), 3.53 (s, 4H), 4.31 (d, J=5.6 Hz, 4H), 4.48 (d, J=5.6 Hz, 4H); $^{13}$C NMR 20.597, 39.375, 75.879, 79.079. Elemental analysis calculated for C$_{10}$H$_{18}$O$_3$: C, 64.49; H, 9.74; Found: C, 64.20; H, 9.63.

EXAMPLE IV

This example illustrates the preparation and properties of the initiator 3,3-bis-[(3-methyl-3-oxetanyl)methyloxymethyl]oxetane.

Sodium hydride (50% dispersion in mineral oil, 32.68 g, 0.681 mol) was washed twice with hexanes and was suspended in 600 mL of DMF. Then, 3-hydroxymethyl-3-methyloxetane (69.46 g, 0.681 mol) was added dropwise over 45 min while hydrogen gas was evolved and a beige solid precipitated. The mixture was stirred for 30 min and a solution of 3,3-bis-(chloromethyl)oxetane (40.61 g, 0.262 mol) in 50 mL of DMF was added. The mixture was heated to 100° C. for 64 h when $^1$H NMR analysis of an aliquot showed that the starting halide had been consumed. The mixture was poured into 600 mL of water and extracted with two portions of 200 mL of methylene chloride. The combined organic extracts were washed with 3 portions of 150 mL of water, dried over magnesium sulfate, and evaporated to give 74.8 g, representing a 91% yield of 3,3-bis-[(3-methyl-3-oxetanyl)methyloxymethyl]oxetane as an oil containing DMF (8.8%). The oil was purified by bulb-to-bulb distillation at 130° C. and 0.1-mm pressure to give 49.83 g, representing a 77% yield, of analytically pure ether.

NMR: $^1$H NMR 1.30 (s, 6H), 3.52 (s, 4H), 3.69 (s, 4H), 4.32 (d, J=5.6 Hz, 4H), 4.45 (s, 4H), 4.48 (d, J=5.6 Hz, 4H); $^{13}$C NMR 21.227, 39.972, 44.138, 72.549, 76.120, 76.527, 79.759. Elemental analysis calculated for $C_{10}H_{18}O_3$: C, 62.91; H, 9.15; Found: C, 63.71; H, 9.32.

EXAMPLE V

This example illustrates the preparation and properties of the initiator 1,4-bis-[(3-methyl-3-oxetanyl)methyloxy]butane.

Sodium hydride (50% dispersion in mineral oil, 29.25 g, 0.609 mol) was washed twice with hexanes and was suspended in 350 mL of DMF. Then, butane-1,4-diol (26.15 g, 0.290 mol) was added dropwise over 20 min while hydrogen gas was evolved and a beige solid precipitated. The mixture was stirred for 30 min and a solution of 3-hydroxymethyl-3-methyloxetane p-toluenesulfonate (148.58 g, 0.58 mol) in 200 mL of DMF was added. The mixture was heated to 60° C. for 24 h and 100° C. for 6 h when $^1$H NMR analysis of an aliquot showed that the starting sulfonate had been consumed. The mixture was poured into 600 mL of water and extracted with three portions of 200 mL of methylene chloride. The combined organic extracts were washed with three portions of 200 mL of water, dried over magnesium sulfate, and evaporated to give 66.5 g, representing an 84% yield of 1,4-bis-[(3-methyl-3-oxetanyl)methyloxy]butane as an oil containing DMF (4%). The oil was purified by bulb-to-bulb distillation at 130° C. and 0.1-mm of pressure to give 60.74 g, representing a 76.7% yield, of analytically pure ether.

NMR: $^1$H NMR 1.29 (s, 6H), 1.66 (p, J=2.7 Hz, 4H), 3.46 (s, 4H), 3.48 (m, 4H), 4.31 (d, J=5.6 Hz, 4H), 4.48 (d, J=5.6 Hz, 4H); $^{13}$C NMR 20.973, 25.927, 39.488, 70.820, 75.578, 79.620. Elemental analysis calculated for $C_{14}H_{26}O_4$: C, 65.09; H, 10.14. Found: C, 65.26; H, 10.15.

EXAMPLE VI

This example illustrates the preparation and properties of the initiator 1,6-bis-[(3-methyl-3-oxetanyl)methyloxy]hexane.

Sodium hydride (50% dispersion in mineral oil, 26.40 g, 0.5498 mol) was washed twice with hexanes and was suspended in 350 mL of DMF. Then, hexane-1,6-diol (30.94 g, 0.2618 mol) was added dropwise over 40 min while hydrogen gas was evolved and a beige solid precipitated. The mixture was stirred for 30 min and a solution of 3-hydroxymethyl-3-methyloxetane p-toluenesulfonate (140.74 g, 0.55 mol) in 150 mL of DMF was added. The mixture was heated to 100° C. for 24 h when $^1$H NMR analysis of an aliquot showed that the starting sulfonate had been consumed. The mixture was poured into 600 mL of water and extracted with three portions of 200 mL of methylene chloride. The combined organic extracts were washed with three portions of 200 mL of water, dried over magnesium sulfate, and evaporated to give 70.35 g, representing an 87% yield, of 1,6-bis-[(3-methyl-3-oxetanyl)methyloxy]hexane as an oil containing DMF (12%). An analytical sample was prepared by bulb-to-bulb distillation at 143° C. and 0.1-mm of pressure.

NMR: $^1$H NMR 1.30 (s, 6H), 1.37 (m, 4H), 1.57 (m, 4H), 3.46 (s, 4H), 3.46 (m, 4H), 4.33 (d, J=5.6 Hz, 4H), 4.50 (d, J=5.6 Hz, 4H); $^{13}$C NMR 21.230, 25.844, 29.384, 39.796, 71.362, 75.922, 80.032. Elemental analysis calculated for $C_{16}H_{30}O_4$: C, 67.10; H, 10.56; Found: C, 66.98; H, 10.62.

EXAMPLE VII

This example illustrates the preparation and properties of the initiator 1,6-bis-[(3-methyl-3-oxetanyl)methyloxy]hexane and 1-[3-methyl-3-oxetanyl)methyloxy]hex-5-ene.

Sodium hydride (50% dispersion in mineral oil, 10.09 g, 0.209 mol) was washed twice with hexanes and was suspended in 250 mL of DMF. Then, 3-hydroxymethyl-3-methyloxetane (21.359 g, 0.2094 mol) was added dropwise over 40 min while hydrogen gas was evolved and a beige solid precipitated. The mixture was stirred for 30 min and 1,6-dibromohexane (21.292 g, 0.0872 mol) was added. The mixture was heated to 110° C. for 24 h when $^1$H NMR analysis of an aliquot showed the dibromide had been consumed. The mixture was poured into 450 mL of water and extracted with three portions of 200 mL of methylene chloride. The combined organic extracts were washed with three portions of 200 mL of water, dried over magnesium sulfate, and evaporated to give 37.9 g of an oil. The residue was distilled to give 2.09 g, representing a 12% yield, of 1-[3-methyl-3-oxetanyl)methyloxy]hex-5-ene, bp 40°–45° C. at 0.15-mm pressure.

NMR: $^1$H NMR 1.22 (s, 3H), 1.37 (q, J=7 Hz, 2H), 1.48 (q, J=7 Hz, 2H), 1.98 (m, J=7 Hz, 2H), 3.38 (2, 2H), 3.38 (t, J=7 Hz, 2H), 4.25 (d, J=5.7 Hz, 2H), 4.42 (d, J=5.7 Hz, 2H), 4.88 (m, 2H), 5.70 (m, 1H); $^{13}$C NMR 21.125, 25.238, 28.776, 33.289, 39.661, 43.450, 71.130, 75.789, 79.421, 79.895, 114.269, 138.427. Elemental analysis calculated for $C_{11}H_{20}O_2$: C, 71.70; H, 10.94; Found: C, 70.77, H, 10.94. The pot residue was found to contain 3.35 g of 1,6-bis-[(3-methyl-3-oxetanyl)methyloxy]hexane identical with that prepared above.

EXAMPLE VIII

This example illustrates the preparation and properties of the initiator 1,4-bis-[(3-chloromethyl-3-oxetanyl)-methyloxy]butane.

Sodium hydride (50% dispersion in mineral oil, 29.29 g, 0.610 mol) was washed twice with hexanes and was suspended in 375 mL of DMF. Then, butane-1,4-diol (23.0 g, 0.277 mol) was added dropwise over 20 rain while hydrogen gas was evolved and a beige solid precipitated. The mixture was stirred for 30 rain and a solution of 3,3-bis-(chloromethyl)oxetane (214.99 g, 1.387 mol) in 150 mL of DMF was added. The mixture was heated to 100° C. for 24 h, and then was poured into 600 mL of water and extracted with three portions of 200 mL of methylene chloride. The combined organic extracts were washed with three portions of 200 mL of water, dried over magnesium sulfate, and evaporated to give 192 g of crude product containing excess starting material. The residue was fractionally distilled to give 57.74 g, representing a 77.5% yield, of 1,4-bis-[(3-chloromethyl-3-oxetanyl)methyloxy]butane, bp 158° C. at 0.1-mm of pressure, mp 49° C.

NMR: $^1$H NMR 1.29 (s, 6H), 1.66 (p, =2.7 Hz, 4H), 3.46 (s, 4H), 3.48 (m, 4H), 4.31 (d, J=5.6 Hz, 4H), 4.48 (d, J=5.6 Hz, 4H); $^{13}$C NMR 20.973, 25.927, 39.488, 70.820, 75.578, 79.620. Elemental analysis calculated for $C_{14}H_{26}O_4$: C, 51.37; H, 7.39, Cl, 21.67. Found: C, 51.27; H, 7.36; Cl, 21.97.

EXAMPLE IX

This example illustrates the preparation and properties of the initiator 1,4-bis-[(3-azidomethyl-3-oxetanyl)-methyloxy]butane.

A mixture of 1,4-bis-[3-chloromethyl-3-oxetanyl)methyloxy]butane (5.00 g, 15.28 mmol) and sodium iodide (5.96 g, 39.7 mmol) in 40 mL of 2-butanone was refluxed for 24 h. The mixture was cooled, filtered and evaporated, and the residue was dissolved in 50 mL of methylene chloride. This solution was washed with three portions of 50 mL of a 5% aqueous sodium thiosulfate solution and 50 mL of water, dried over magnesium sulfate, and evaporated to give 6.90 g, representing an 89% yield, of 1,4-bis-[(3-iodomethyl-3-oxetanyl)methyloxy]butane, mp 51°-52° C. An analytical sample was prepared by recrystallization from hexanes, mp 51°.

NMR: $^1$H NMR 1.63 (q, J=7 Hz, 4Hz), 3.50 (m, 4H), 3.59 (s, 4H), 3.69 (s, 4H), 4.34 (d, J=5.7 Hz, 4H), 4.38 (d, J=5.7 Hz, 4H); $^{13}$C NMR 43.776, 54.152, 71.234, 72.115, 76.697. Elemental analysis calculated for $C_{14}H_{24}O_4I_2$: C, 32.96; H, 4.74. Found: C, 32.60; H, 4.79.

EXAMPLE X

This example illustrates the preparation and properties of the initiator 1,4-bis-[(3-nitratomethyl-3-oxetanyl)-methyloxy]butane.

A mixture of 1,4-bis-[(3-iodomethyl-3-oxetanyl)methyloxy]butane (5.0 g, 9.80 mmol) and silver nitrate (3.66 g, 21.5 mmol) was stirred in 40 mL of acetonitrile for 5 days at ambient temperature. The mixture was poured into 50 mL of water, filtered, and extracted with two portions of 50 mL of methylene chloride. The combined organic extracts were washed with 100 mL of water, dried over magnesium sulfate and evaporated to give 3.62 g, representing a 97% yield, of 1,4-bis-[(3-nitratomethyl-3-oxetanyl)methyloxy]butane, mp 58°-63° C. An analytical sample was prepared by recrystallization from ethanol, mp 66°-67° C.

NMR: $^1$H NMR 1.60 (m, 4H), 3.47 (m, 4H), 3.67 (s, 4H). 4.34 (d, J=5.7 Hz, 4H), 4.40 (d, J=5.7 Hz, 4H) 4.5 (s, 4H); $^{13}$C NMR 26.052, 42.293, 71.2452, 71.408, 73.262, 75.754. Elemental analysis calculated for $C_{14}H_{24}N_2O_{10}$: C, 44.2; H, 6.37, N, 7.37. Found: C, 44.38; H, 6.47; N, 7.41.

EXAMPLE XI

This example illustrates the preparation and properties of the initiator 1,4-bis-[(3-azidomethyl-3-oxetanyl)-methyloxy]butane.

A mixture of 1,4-bis-[3-chloromethyl-3-oxetanyl)methyloxy]butane (10.00 g, 30.5 mmol) and sodium azide (4.37 g, 67.2 mmol) in 150 mL of DMF was heated at 67°-73° C. for 48 h. The mixture was cooled, poured into 600 mL of water, and filtered. The solid was washed with water and dried in vacuo to give 8.19 g, representing a 79% yield, of 1,4-bis-[(3-azidomethyl-3-oxetanyl)methyloxy]butane, mp 59.12° C.

NMR: $^1$H NMR 1.61 (m, 4H), 3.46 (m, 4H), 3.62 (s, 4H), 3.65 (s, 4H), 4.41 (s, 8H); $^{13}$C NMR 26.214, 43.776, 54.152, 71.234, 72.116, 76.697. Elemental analysis calculated for $C_{14}H_{24}N_6O_4$: C, 49.40; H, 7.11, N, 24.69; Found: C, 49.32; H, 7.10; N, 24.37.

EXAMPLE XII

This example illustrates the preparation and properties of the star polymer formed from the initiator 1,1,1-tris-[(3-methyl-3-oxetanyl)methoxymethyl]propane and the oxetane monomer 3-nitratomethyl-3-methyloxetane (NMMO).

A solution of butane-1,4-diol (690 mg, 7.8 mmol) and boron trifluoride etherate (1.919 mL, 15 mmol) in 100 mL of methylene chloride was stirred at ambient temperature for 15 min under nitrogen in a dry polymerization flask. The solution was cooled to 0° C. and a solution of 3-nitratomethyl-3-methyloxetane (50.0 g, 0.34 mol) and 1,1,1-tris-[(3-methyl-3-oxetanyl)methyloxymethyl]propane (1.0 g, 2.6 mmol) in 70 mL of methylene chloride was added over 1.25 h. The resultant solution was stirred for 2 h at 10° C. at which time $^1$H NMR analysis of an aliquot indicated that the reaction was 86% complete. The reaction was quenched with 50 mL of water. Then, 200 mL of methanol was added and the organic layer was decanted from the polymer that had precipitated as an oil. The oil was washed with methanol and dried for 24 h in vacuo (2 mm) to give 40.05 g, representing a 75% yield, of an amorphous oil.

Gel Permeation Chromatography (GPC) (THF): Number average molecular weight (Mn) 4,368, Weight average molecular weight (Mw) 6,320. Polydispersity (Disp.): 1.45. NMR: $^1$H NMR 0.88, 0.94, 1.00, 1.05 1.10(s), 1.31, 3.35 (d, J=8 Hz) 3.40 (d, J=8 Hz), 3.65 (q, J=7 Hz), 4.44, 4.51, 4.57.; $^{13}$C NMR 9.965, 17.072, 17.453, 22.200, 26.644, 40.354, 40.622, 41.480, 66.605, 71.669, 71.669, 71.812, 72.495, 73.233, 73.905, 75.063, 75.476, 76.481.

EXAMPLE XIII

This example illustrates the preparation and properties of the star polymer formed from the initiator 1,6-bis-[(3-methyl-3-oxetanyl)methyloxy]hexane and the oxetane monomer 3,3-bis-(ethoxymethyl)oxetane (BEMO).

A solution of butane-1,4-diol (258 mg, 2.87 mmol) and boron trifluoride etherate (0.815 g, 5.75 mmol) in 50 mL of methylene chloride was stirred at ambient temperature for 15 min under nitrogen in a dry polymerization flask. The solution was cooled to 0° C. and a solution of 3,3-bis-(ethoxymethyl)oxetane (25.0 g, 0.14 mol) and 1,6-bis-[(3-methyl-3-oxetanyl)methyloxy]hexane (0.410 g, 1.4 mmol) in 50 mL of methylene chloride was added over 25 min. The resultant solution was stirred for 1.5 h at 15° C. at which time $^1$H NMR analysis of an aliquot indicated that the reaction was complete. The solution was quenched with 50 mL of water and washed with two portions of 100 mL of water. Then, 600 mL of methanol was added and the organic layer was decanted from the polymer that had precipitated as an oil. The oil was washed with methanol and dried for 24 h in vacuo (2 mm) to give 16.8 g, representing a 67% yield, of a solid.

GPC (THF): Mn 4,368, Mw 6,320. Polydispersity: 1.47. NMR: $^1$H NMR 3.39–3.45 (m, 6H), 4.45 (s, 2H).

EXAMPLE XIX

This example illustrates the preparation and properties of the star polymer formed from the concurrent addition of initiator 1,1,1-tris-[(3-methyl-3-oxetanyl)methoxymethyl]propane and the oxetane monomer 3,3-bis-(azidomethyl)oxetane (BAMO).

A solution of butane-1,4-diol (59.2 mg, 0.65 mmol) and boron trifluoride etherate (190 mg, 1.34 mmol) in 8 mL of methylene chloride was stirred at ambient temperature for 30 min under nitrogen in a dry polymerization flask. The solution was cooled to 1° C. and a solution of 1,1,1-tris-[(3-methyl-3-oxetanyl)methoxymethyl]propane (175 mg, 0.453 mmol) and 3,3-bis-(azidomethyl)oxetane (2.008 g, 11.95 mmol) in 10 mL of methylene chloride was added. The resultant solution was stirred for 1 h at 2° C. and then warmed to ambient for 16 h. The solution was quenched with 50 mL of water and washed with 2 portions of 50 mL of brine. Then, the solution was added to 110 mL of methanol and the solvents were decanted. The residue was washed with methanol and dried in vacuo to give 1.7 g, representing an 87% yield, of a semi-crystalline solid.

GPC (THF) showed four peaks with Mn 2,818, Mw 4,164. Polydispersity: 1.48. Differential scanning calorimetry (DSC) showed a broad endotherm at 30°–80° C. and an onset of decomposition at 200° C. Heat Flow: 2,599 J/g. NMR: $^1$H NMR 0.85 (s), 0.91 (s), 1.35 (m), 1.61 (m), 1.93 (m), 3.27–3.58 (m); NMR (TFAA) 17.72, 45.49, 45.73.51.22, 51.29, 52.06, 66.48, 69.14, 69.65, 70.39, 70.83.

EXAMPLE XV

This example illustrates the preparation and properties of the star polymer formed from the sequential addition of the initiator 1,1,1-tris-[(3-methyl-3-oxetanyl)methoxymethyl]propane and the oxetane monomer 3,3-bis-(azidomethyl)oxetane (BAMO).

A solution of butane-1,4-diol (106 mg, 1.18 mmol) and boron trifluoride etherate (346 mg, 2.44 mmol) in 15 mL of methylene chloride was stirred at ambient temperature for 30 min under nitrogen in a dry polymerization flask. The solution was cooled to 1° C. and a solution of 1,1,1-tris-[(3-methyl-3-oxetanyl)methoxymethyl]propane (156 mg, 0.40 mmol) in methylene chloride (19.8 g) was added and the mixture was stirred for 10 minutes at 1.5° C. Next, neat 3,3-bis-(azidomethyl) oxetane (2.003 g, 11.93 mmol) was added over 5 min. The resultant solution was stirred for 1 h at 2° C. and then warmed to ambient temperature for 24 h. The solution was quenched with 50 mL of water and washed with two portions of 50 mL of brine. Then, the solution was added to 110 mL of methanol and the solvents were decanted. The residue was washed with methanol and dried in vacuo to give 0.550 g, representing a 26% yield, of an oil.

GPC (THF) showed one peak, Mn 2,730. Polydispersity: 1.38. NMR: $^1$H NMR 0.85 (s), 0.91 (s), 1.35 (m), 1.61 (m), 1.93 (m), 3.27–3.58 (m); $^{13}$C NMR (TFAA) 17.72, 45.49, 45.73, 51.22, 51.29, 52.06, 66.48, 69.14, 69.65, 70.39, 70.83.

EXAMPLE XVI

This example illustrates the preparation and properties of the star polymer formed from the initiator 1,4-bis-[(3-azidomethyl-3-oxetanyl)methyloxy]butane and the oxetane monomer 3,3-bis-(ethoxymethyl)oxetane (BEMO).

A solution of trifluoroethanol (100 mg, 1.0 mmol) and boron trifluoride etherate (142 mg, 1.0 mmol) in 10 mL of methylene chloride was stirred at ambient temperature for 15 min under nitrogen in a dry polymerization flask. The solution was cooled to 22° C. and a solution of 1,4-bis-[(3-azidomethyl-3-oxetanyl)methyloxy]butane (101 mg, 0.297 mmol) in 5 mL of methylene chloride was added. Subsequently, a solution of 3,3-bis-(ethoxymethyl)oxetane (1.534 g, 8.82 mmol) in 5 mL of methylene chloride was added dropwise. The resultant solution was stirred for 0.5 h at −22° C. and then warmed to ambient temperature for 16 h. The solution was quenched with 50 mL of water and washed with two portions of 50 mL of brine. Then, the solution was dried over magnesium sulfate and the solvent was evaporated in vacuo to give 1.45 g, representing an 86% yield, of an amorphous rubber.

GPC (THF): Mn 4,850, Mw 4,928. Polydispersity: 1.18. Differential Scanning Calorimetry showed a mp of 76.1° C. NMR: $^1$H NMR 1.13–1.25 (m), 1.60 (s), 3.34.3.44 (m); $^{13}$C NMR 15.13, 25.98, 29.65, 44.78, 45.56, 45.82, 51.92, 66.28, 66.65, 66.91, 68.87, 69.00, 69.72, 70.38, 70.79.

EXAMPLE XVII

This example illustrates the preparation and properties of the star homopolymer formed from the initiator 1,4-bis-[(3-azidomethyl-3-oxetanyl)methyloxy]butane.

A solution of trifluoroethanol (47 mg, 0.47 mmol) and boron trifluoride etherate (66.6 mg, 0.47 mmol) in 5 mL of methylene chloride was stirred at ambient temperature for 25 min under nitrogen in a dry polymerization flask. The solution was cooled to −20° C. and a solution of 1,4-bis-[(3-azidomethyl-3-oxetanyl)methyloxy]butane (270 mg, 0.80 mmol) in 5 mL of methylene chloride was added over 10 min. and the solution was stirred for 16 h at −20° C., at which time essentially no polymer formation was detected by NMR analysis. The solution was stirred at −10° C. for 64 h during which time 95% of the monomer was converted to polymer as determined by NMR analysis. The reaction mixture was warmed to 3° C. and was quenched with 50 mL of water. The organic layer was washed with two portions of 50 mL of brine, was dried over magnesium sulfate, and the solvent was evaporated in vacuo to give an amorphous rubber that became insoluble upon standing.

GPC (THF): Mn 3,469, Mw 5,247. Polydispersity 1.51. Differential Scanning Calorimetry showed a mp of 45.2° C. (90.92 J/g), decomposition at 231.7° C. (1126 J/g); NMR: $^1$H NMR 1.63 (s), 3.32–3.29 (m), 3.46 (s) 3.48 (s).

EXAMPLE XVIII

This example illustrates the preparation and properties of the star polymer formed from the initiator 1,4-bis-[(3-azidomethyl-3-oxetanyl)methyloxy]butane and the oxetane monomer 3,3-bis-(azidomethyl)oxetane (BAMO).

A solution of trifluoroethanol (217 mg, 2.17 mmol) and boron trifluoride etherate (325 mg, 2.29 mmol) in 5 mL of methylene chloride was stirred at ambient temperature for 30 min under nitrogen in a dry polymerization flask. The solution was cooled to 0° C. and a solution of 1,4-bis-[(3-azidomethyl-3-oxetanyl)methyloxy]-butane (373 mg, 1.09 mmol) and 3,3-bis-(azidomethyl)oxetane (3.67 g, 21.8 mmol) in 25 mL of methylene chloride was added over 30 min, and the solution was stirred for 16 h at 0° C., during which time 93% of the monomers were converted to polymer as determined by NMR analysis. The reaction mixture was warmed to 3° C. and was quenched with 50 mL of water. The organic layer was washed with two portions of 50 mL of brine and was dried over magnesium sulfate. The solvent was evaporated in vacuo to give 3.0 g, representing a 75% yield, of an amorphous rubber.

GPC (THF): Mn 3,974, Mw 7,002. Polydispersity: 1.76. NMR: $^1$H NMR 1.62 (s) 3.27–3.56 (m); $^{13}$C 25.96, 26.34, 45.19, 45.45, 45.65, 51.00, 51.32, 51.77, 62.81, 68.85, 69.58, 70.10, 70.96, 71.28.

The foregoing is offered for purposes of illustration. It will be readily apparent to those skilled in the art that the operating conditions, materials, procedural steps and other parameters of the systems described herein may be further modified or substituted in various ways without departing from the spirit and scope of the invention.

What is claimed is:

1. A process for the preparation of a star polymer, said process comprising:
   (a) forming an initiator compound by reacting a preinitiator precursor with a catalyst, said preinitiator precursor being an organic compound capable of forming an adduct with said catalyst, and said catalyst being a substance capable of causing cationic polymerization;
   (b) combining said initiator compound with a multi-oxetane compound to form an initiating species;
   (c) contacting said initiating species with a monomer capable of cationic polymerization; and
   (d) allowing polymerization to proceed by chain elongation until the supply of available monomer is substantially exhausted.

2. A process in accordance with claim 1 in which said preinitiator precursor is a polyol.

3. A process in accordance with claim 2 in which said preinitiator precursor is a diol.

4. A process in accordance with claim 1 in which said catalyst is a strong acid.

5. A process in accordance with claim 4 in which said catalyst is a Lewis acid selected from the group consisting of $AlCl_3$, $BF_3$, $TiCl_4$, $ZnI_2$, $SiF_4$, $SbF_5$, $PF_5$, $AsF_5$, and $SbU_5$.

6. A process in accordance with claim 1 in which said monomer is a cyclic ether having 2 to 5 carbon atoms in the ether ring.

7. A process in accordance with claim 6 in which said cyclic ether is an oxetane having the formula

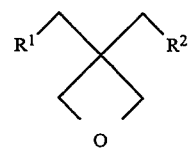

in which $R^1$ and $R^2$ are members independently selected from the group consisting of H, lower alkyl, lower alkoxy, Br, Cl, I, $NF_2$, $ONO_2$, $NO_2$, $N_3$, and $N(R^3)NO_2$, where $R^3$ is H or a lower alkyl.

8. A process in accordance with claim 7 in which said oxetane is 3-nitratomethyl-3-methyloxetane.

9. A process in accordance with claim 7 in which said oxetane is 3,3-bis-(azidomethyl)oxetane.

10. A process in accordance with claim 7 in which said oxetane is 3,3-bis-(ethoxymethyl)oxetane.

* * * * *